United States Patent
Roberts et al.

(10) Patent No.: US 9,295,787 B2
(45) Date of Patent: Mar. 29, 2016

(54) ADAPTER MEANS FOR USE IN COMBINATION WITH A PRE-FILLED SYRINGE AND A SAFETY DEVICE, SAFETY DEVICE AND INJECTION DEVICE

(75) Inventors: Gareth Roberts, Wrexham (GB); Sioned Owen, Denbigh (GB); Matthew Ekman, Cheshire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 144 days.

(21) Appl. No.: 13/976,417

(22) PCT Filed: Dec. 30, 2011

(86) PCT No.: PCT/EP2011/074274
§ 371 (c)(1),
(2), (4) Date: Jun. 26, 2013

(87) PCT Pub. No.: WO2012/093069
PCT Pub. Date: Jul. 12, 2012

(65) Prior Publication Data
US 2013/0274678 A1    Oct. 17, 2013

(30) Foreign Application Priority Data
Jan. 4, 2011 (EP) .................................... 11150074

(51) Int. Cl.
*A61M 5/32*     (2006.01)
*A61M 5/28*     (2006.01)

(52) U.S. Cl.
CPC ............. *A61M 5/3243* (2013.01); *A61M 5/326* (2013.01); *A61M 5/3271* (2013.01); *A61M 5/28* (2013.01); *A61M 2005/3247* (2013.01)

(58) Field of Classification Search
CPC .......... A61M 2005/3247; A61M 5/28; A61M 5/3243; A61M 5/326; A61M 5/3271
See application file for complete search history.

(56) References Cited

U.S. PATENT DOCUMENTS

2012/0022466 A1* 1/2012 James et al. ................. 604/198
2013/0331796 A1* 12/2013 Wozencroft ................. 604/197

FOREIGN PATENT DOCUMENTS

| EP | 1970086 A2 | 9/2008 |
| WO | 2005009519 A1 | 2/2005 |
| WO | 2007047200 A1 | 4/2007 |
| WO | 2010104779 A1 | 9/2010 |

* cited by examiner

*Primary Examiner* — Rebecca E Eisenberg
(74) *Attorney, Agent, or Firm* — Fish & Richardson P.C.

(57) ABSTRACT

According to the invention, an adaptor means for use in combination with a pre-filled syringe and a safety device for the pre-filled syringe is adapted to affix the pre-filled syringe thereto, whereby the adaptor means engages a barrel of the pre-filled syringe. The adaptor means comprises at least one locking projection that is adapted to lock the adaptor means to the safety device.

11 Claims, 4 Drawing Sheets

ADAPTER MEANS FOR USE IN COMBINATION WITH A PRE-FILLED SYRINGE AND A SAFETY DEVICE, SAFETY DEVICE AND INJECTION DEVICE

CROSS REFERENCE TO RELATED APPLICATIONS

The present application is a U.S. National Phase Application pursuant to 35 U.S.C. §371 of International Application No. PCT/EP2011/074274 filed Dec. 30, 2011, which claims priority to European Patent Application No. 11150074.0 filed Jan. 4, 2011. The entire disclosure contents of these applications are herewith incorporated by reference into the present application.

FIELD OF INVENTION

The present invention generally relates to safety devices that provide needle safety and more particularly to safety devices for pre-filled syringes. An adaptor means is provided that is adapted to mount a pre-filled syringe within the safety device. The safety device is adapted to avoid accidental needle pricks and needle injuries before, during and after an injection of a medication or drug contained in the pre-filled syringe. In particular, the safety device provides needle safety for a subcutaneous self-administrated injection or for an injection administered by a health-care professional. The present invention further relates to injection devices comprising a pre-filled syringe.

BACKGROUND

Pre-filled syringes that are filled with a selected dosage of a medication are well known injection devices for administering the medication to a patient. Safety devices for covering a needle of a pre-filled syringe before and after use are also well known. Typically, these devices comprise a needle shield that is either manually moved or moved by the action of a relaxing spring to surround the needle.

A different type of safety device known in the state of the art achieves the object of providing needle safety by arranging the pre-filled syringe movable relative to a body, where the pre-filled syringe is retracted into the body after the injection.

WO 2010/104779 A1 discloses a pharmaceutical delivery apparatus with an automatic syringe reaction following a manually controlled injection. The apparatus includes a housing, a syringe carriage, a medication-filled syringe held within the carriage, the syringe needle tip being disposed within the housing in a first position and projecting from the housing beyond the housing proximal end for insertion into an injection site in a second position, a manually shift table plunger, means on the carriage and the housing and the plunger for causing the carriage to advance from the first position to the second position and for injecting medicine from the syringe when the plunger is manually plunged proximally toward the housing, and means on the carriage and the plunger for causing the carriage to retract from the second position to a position at which the needle tip is disposed within the housing when the ;plunger shifts distally.

SUMMARY

It is an object of the present invention to provide an improved injection device that prevents accidental needle stick injuries.

The object is achieved by an adaptor means according to claim 1.

Preferred embodiments of the invention are given in the dependent claims.

In the context of this specification, the terms distal and proximal are defined from the point of view of a person performing an injection. Consequently, a distal direction refers to a direction pointing towards the body of a patient receiving an injection and a distal end defines an end of an element that is directed towards the body of the patient. Respectively, the proximal end of an element or the proximal direction is directed away from the body of the patient receiving the injection and opposite to the distal end or distal direction.

According to the invention, an injection device comprises a pre-filled syringe and a safety device for the pre-filled syringe. The safety device comprises
  an adaptor means,
  a hollow support body and
  a hollow outer body slidably arranged with respect to the support body.

The adaptor means is adapted to affix the pre-filled syringe thereto, whereby the adaptor means engages a barrel of the pre-filled syringe. The adaptor means comprises at least one locking projection that is adapted to lock the adaptor means to the safety device.

The injection device advantageously combines the aforementioned advantages for the safety device and the adaptor means. The injection device is easy to handle and prevents accidental needle stick injuries before, during and after an injection delivering a medication or drug beneath the skin of the patient.

The adaptor means comprises inner dimensions that are suitable to engage and affix the barrel of the pre-filled syringe to the adaptor means. The adaptor means comprises outer dimensions designed to securely mount the adaptor means and the pre-filled syringe affixed thereto within the safety device. It is within the scope of the present invention to provide different adaptor means with different inner dimensions and same outer dimensions, so that pre-filled syringes of different sizes may be retained in the safety device. This reduces production costs, as the main components of the safety device may be produced in large quantities independently of a specific medical application requiring a pre-filled syringe of a certain size or type.

Furthermore, the locking projection of the adaptor collar provides a means to securely lock the pre-filled syringe retained within the adaptor collar in a position within the safety device providing needle safety, whereby a re-exposure of a used hypodermic needle of the pre-filled syringe is prevented.

The adaptor means may have an axial dimension substantially corresponding to an axial length of a barrel of the pre-filled syringe. The adaptor collar provides a platform substantially along the entire axial length of the barrel that may be engaged by safety features of the safety device, like for example a mounting means mounting the pre-filled syringe to the safety device, a retraction mechanism for the pre-filled syringe ensuring needle safety or a mechanism preventing a re-exposure of a used hypodermic needle.

According to a possible embodiment of the invention, two opposing clamp arms of the adaptor means are adapted to frictionally engage the barrel of the pre-filled syringe to affix the pre-filled syringe to the adaptor means. The clamp arms provide a simple means to firmly retain the pre-filled syringe within and affix the pre-filled syringe to the adaptor means.

The adaptor means may comprise a central aperture with an inner diameter corresponding to an outer diameter of the barrel of the pre-filled syringe. In particular, differently sized pre-filled syringes may comprise barrels with different outer diameters, wherein each of the differently sized pre-filled syringes is affixable to one correspondingly sized adaptor collar. The adaptor collar may thus be used as a spacer element for the safety device, so that the safety device may comprise dimensions that are essentially independent of the dimensions of the pre-filled syringe mounted within the safety device via the adaptor means.

According to a possible embodiment of the invention, the adaptor means comprises a proximal collar adapted to abut a barrel collar of the barrel. The proximal collar thus avoids a displacement of the pre-filled syringe with respect to the adaptor means in at least the distal direction.

According to another possible embodiment of the invention, two locking projections project radial outwards from two opposite sides of the adaptor means to securely lock the adaptor collar and the pre-filled syringe affixed thereto in a needle-safe position.

According to the invention, the safety device for a pre-filled syringe comprises
the adaptor means,
the hollow support body and
the hollow outer body slidably arranged with respect to the support body.

The adaptor means is adapted to affix the pre-filled syringe thereto. The adaptor means is retained within the support body in a manner that the adaptor means is movable with respect to the support body from a first position to a second position, wherein the locking projection of the adaptor means engages a locking recess formed into the support body to irreversibly lock the adaptor means in the second position.

The safety device with the adaptor means advantageously combines the aforementioned advantages and prevents accidental needle stick injuries in particular after an injection has been performed. The locking projection and the locking recess constitute a particularly simple means to lock the adaptor to the retracted second position. The locking recess may have the shape of an aperture formed into the support body of the safety device. Alternatively, the locking recess may be formed into an inner surface of the support body to prevent a person from tampering with the locking projection locking the adaptor means in the second position.

According to a possible embodiment of the invention, a radial projection of the outer body protrudes radially inwards and through a longitudinal slot formed into the support body. The radial projection catches a distal collar of the adaptor means to couple the adaptor means to the outer body. The radial projection moves along the longitudinal slot when the outer body is slid with respect to the support body, so that a relative rotation between outer body and support body is prevented. The outer body thus conveniently slides in a linear translatory motion, whereby in particular an unpleasant rotation of parts that may abut the skin of the patient receiving the injection is prevented. Furthermore, the radial projection catching the distal collar provides a reliable and efficient mechanism to retract the adaptor collar mounting the pre-filled syringe to the second position, wherein, in the second position, the support body surrounds the hypodermic needle of the pre-filled syringe to avoid accidental needle stick injuries.

The adaptor means coupled to the outer body may be movable from the first position to the second position by a proximal movement of the outer body with respect to the support body. The retraction of the pre-filled syringe may thus be accomplished by manually actuating the outer body in case an automatic retraction mechanism of the safety device fails.

According to another possible embodiment of the invention, a spring means is arranged within the safety device to bias the outer body with respect to the support body in a proximal direction. The spring means biasing the outer body automatically retracts the adaptor means coupled to the outer body from the first position to the second position when the injection is completed. A further interaction of the user of the safety device to ensure needle safety is not required.

The spring means may be arranged within the safety device in a non-energized or only slightly energized state, so that material fatigue is avoided. The safety device may thus be reliably used even after prolonged periods of storage.

Furthermore, the pre-filled syringe is affixed to the adaptor means that is retained within the support body in the first position. In the first position, a hypodermic needle of the pre-filled syringe projects distally from the support body. The pre-filled syringe affixed to the adaptor means is movable with respect to the support body from the first position to the second position. In the second position, the hypodermic needle of the pre-filled syringe is surrounded by the support body. The locking projection of the adaptor means engages the locking recess formed into the support body to irreversibly lock the adaptor means in the second position.

According to a possible embodiment of the invention, the outer body is moveable with respect to the support body in the distal direction to perform an injection stroke, whereby the medication or drug contained in an inner cavity of the pre-filled syringe is expelled through the hypodermic needle. The outer body abuts a piston rod connected to a piston to expel the medication. Alternatively, the piston rod is integrated to the outer body. The outer body may be conveniently gripped by a user and be pushed in a single linear injection stroke towards the skin surface of a patient allowing for a use of the injection device even by an inexperienced user.

Details of the present invention are described hereinafter. However, it should be understood that the detailed description and the specific examples indicate possible embodiments of the invention and are given by way of illustration only. Various changes and modifications of the illustrated embodiments within the spirit and scope of the invention are appreciated by those skilled in the art.

BRIEF DESCRIPTION OF THE DRAWINGS

The present invention will be better understood from the detailed description given in the following. The accompanying drawings are given for illustrative purposes only and do not limit the scope of the present invention.

Corresponding parts are marked with the same reference symbols in all figures.

DETAILED DESCRIPTION

Figure 1:
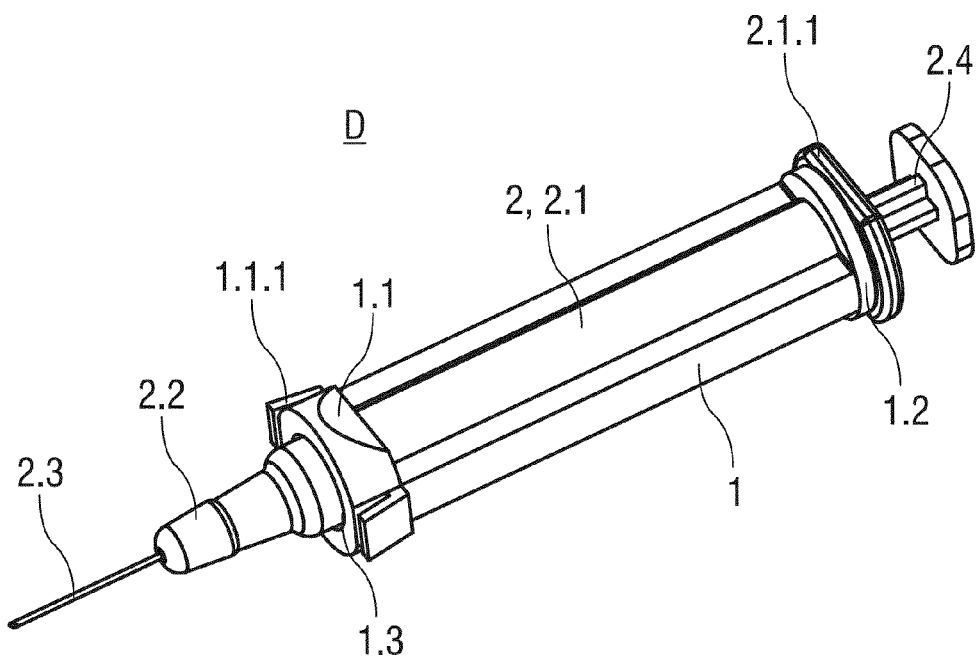
FIG. 1 shows a perspective view of an adaptor means with a pre-filled syringe affixed thereto.

FIG. 1 shows an adaptor means 1 for use in combination with a pre-filled syringe 2 and a safety device 3 for a pre-filled syringe 2. The pre-filled syringe 2 is mounted within the adaptor means 1 that extends over a substantial axial length of a barrel 2.1 of the pre-filled syringe 2. The adaptor means 1 comprises a distal collar 1.1 protruding in a radial outward direction and a proximal collar 1.2 abutting a barrel collar 2.1.1 of the barrel 2. The adaptor means 1 fits tightly over the barrel 2.1 and frictionally engages the barrel 2.1 to mount the pre-filled syringe 2 within the adaptor means 1.

A nozzle 2.2 protrudes the adaptor means 1 in a distal direction. A hypodermic needle 2.3 of the pre-filled syringe 2 is affixed to the nozzle 2.2. A piston rod 2.4 protrudes the barrel 2.1 in the proximal direction. The adaptor means 1 comprises a central aperture 1.3 with an inner diameter that corresponds to an outer diameter of the barrel 2.1 of the pre-filled syringe 2. The pre-filled syringe 2 is mounted between two opposing clamp arms 1.4 that frictionally engage the barrel 2.1.

Alternatively, the adaptor means 1 may be of substantially cylindrical shape with an inner diameter that corresponds to the outer diameter of the barrel 2.1, wherein an inner surface of the substantially cylindrical adaptor means 1 engages the barrel 2.1 of the pre-filled syringe 2.

At least one locking projection 1.1.1 projects from the distal collar 1.1 of the adaptor means 1 in the radial outward direction. The locking projection 1.1.1 is resiliently deflectable and adapted to lock the adaptor means 1 to a safety device 3 providing needle safety for the pre-filled syringe 2 after an injection.

Alternatively, the locking projection 1.1.1 may project from the clamp arms 1.4 or the proximal collar 1.2 of the adaptor means 1.

FIG. 1 shows a distal collar 1.1, wherein two radial outwardly protruding locking projections 1.1.1 are formed to opposite sides of the distal collar 1.1. The adaptor means 1 is made from a resilient plastics material like a polymer, an elastomer or more particularly a silicone elastomer.

Figure 2:
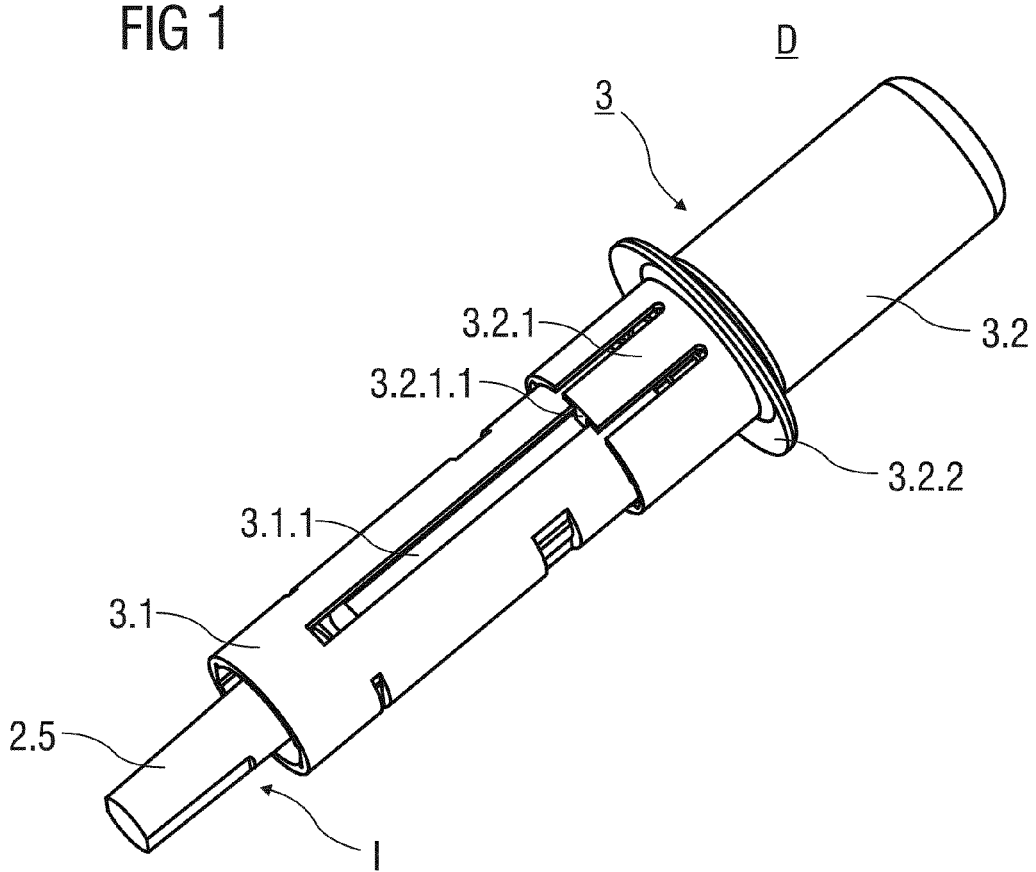
FIG. 2 shows a perspective view of an injection device before use.

FIG. 2 shows a perspective view of an injection device D comprising the pre-filled syringe 2 and a safety device 1 prior to use. The pre-filled syringe 1 is retained within the adaptor means 1 that is mounted within the safety device 3. The safety device 3 comprises a hollow support body 3.1 and a hollow outer body 3.2. The outer body 3.2 is slidably arranged with respect to the support body 3.1. During the injection, the outer body 3.2 moves with respect to the support body 3.1 in the distal direction to actuate the piston rod 2.4 of the pre-filled syringe 2, whereby a medication contained within an inner cavity 2.1.2 of the barrel 2.1 is expelled.

Alternatively, the piston rod 2.4 may be integrated to the outer body 1.3.

The support body 3.1 comprises at least one longitudinal slot 3.1.1 extending over a substantial axial length of the support body 3.1. The longitudinal slot 3.1.1 accommodates a radial projection 3.2.1.1 formed to a flexible arm 3.2.1 of the outer body 3.2. The flexible arm 3.2.1 is integrated to the outer body 3.2 and is resiliently deflectable in the radial outward direction. The radial projection 3.2.1.1 moves along the longitudinal slot 3.1.1 when the outer body 3.2 is moved with respect to the support body 3.1 to perform an injection stroke.

A circumferential gripping means 3.2.2 is formed to an outer surface of the outer body 3.2. The gripping means 3.2.2 supports the hand of a user in carrying out the injection stroke, whereby the outer body 3.2 is manually pushed in the distal direction with respect to the support body 3.1.

The pre-filled syringe 2 is affixed to the adaptor means 1 that is retained within the support body 3.1, so that the hypodermic needle 2.3 protrudes the support body in the distal direction. Prior to use of the injection device D, the hypodermic needle 2.3 is covered by a needle cap 2.5 that is frictionally affixed to the nozzle 2.2 of the pre-filled syringe.

Additionally, the support body 3.1 may comprise a flange (not illustrated) that provides an increased surface area and is adapted to rest onto the skin of a patient during the injection.

The inner dimension of the adaptor means 1 and, in particular, the inner diameter of the central aperture 1.3 corresponds to the outer dimension of the pre-filled syringe 2 and, in particular, the outer diameter of the barrel 2.1. It is within the scope of the present invention to provide different adaptor means 1 that comprise inner dimensions adapted to outer dimensions of pre-filled syringes 2 of various sizes, so that the pre-filled syringe 2 may be firmly retained in the adaptor means 1. The outer dimensions of the different adaptor means 1 are the same and correspond to the inner dimensions of the support body 1.2, so that the adaptor means 1 can be mounted within the support body 3.1. The adaptor means 1 thus acts as a spacer element that allows for a mounting of one of the pre-filled syringes of various sizes within the support body 3.1 of the safety device 3. The dimensions of the main components of the safety device 3 that comprises the support body 3.1 and the outer body 3.2 may thus be chosen essentially independent of the outer dimensions of the pre-filled syringe 2.

Figure 3:
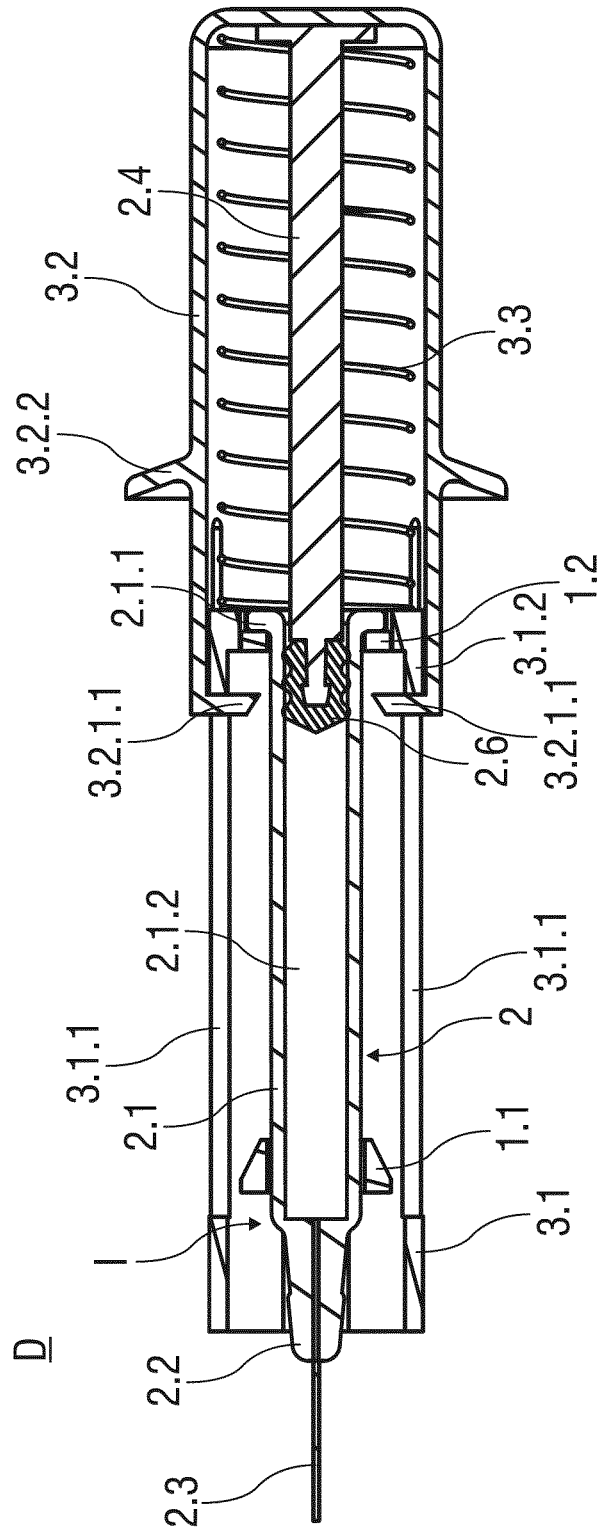
FIG. 3 shows a sectional view of an injection device with a pre-filled syringe affixed to an adaptor means retained in a first position.

FIG. 3 shows a sectional view of the injection device D before the medication or drug contained in the inner cavity 2.1.2 is delivered beneath the skin of the patient. The proximal collar 1.2 of the adaptor means 1 abuts two opposing and radial inwardly protruding inner ribs 3.1.2 formed to an inner surface of the support body 3.1. The inner ribs 3.1.2 mount the adaptor means 1 to the support body 3.1 in a manner that allows a movement of the adaptor means 1 and the pre-filled syringe 2 retained therein from the first position I in a proximal direction.

Two longitudinal slots 3.1.1 are formed in opposite sides of the support body 3.1. Each longitudinal slot 3.1.1 receives one radial projection 3.2.1.1 that moves along the longitudinal slot 3.1.1 when the injection stroke is carried out, whereby a relative rotation of outer body 3.2 with respect to the support body 3.1 is prevented. The radial projection 3.2.1.1 protrudes through the longitudinal slot 3.1.1, so that the distal collar 1.1 of the adaptor means 1 may be engaged by the radial projection 3.2.1.1 at the end of the injection stroke.

Before the injection is performed, the radial projection 3.2.1.1 abuts the inner rib 3.1.2 of the support body 3.1 to limit a proximal movement of the outer body 3.2 with respect to the support body 3.1.

The piston rod 2.4 is connected to a piston 2.6 fluid-tightly sealing a proximal end of the inner cavity 2.1.2. The piston rod 2.4 abuts a proximal surface of the outer body 3.2, so that the piston rod 2.4 and the piston 2.6 may be moved by manually pushing the outer body 3.2 in the distal direction, whereby the medication expelled through the hypodermic needle 2.3 of the pre-filled syringe 2.

A spring means 3.3 is arranged with the safety device 3 that biases the outer body 3.2 with respect to the support body 3.1 in the proximal direction. Initially, the spring means 3.3 is arranged in a non-energized or only slightly energized state within the safety device 3. The spring means 3.3 shown in FIG. 3 is implemented as a conventional compression spring that bears against the support body 3.1 in the distal direction and against the outer body 3.2 in the proximal direction. The compression spring is made from a metal.

Alternatively, the spring means 3.3 may be made from a plastics material to reduce production costs. The spring means 3.3 may have a different shape and design suitable for biasing the outer body 3.2 in the proximal direction.

Figure 4:
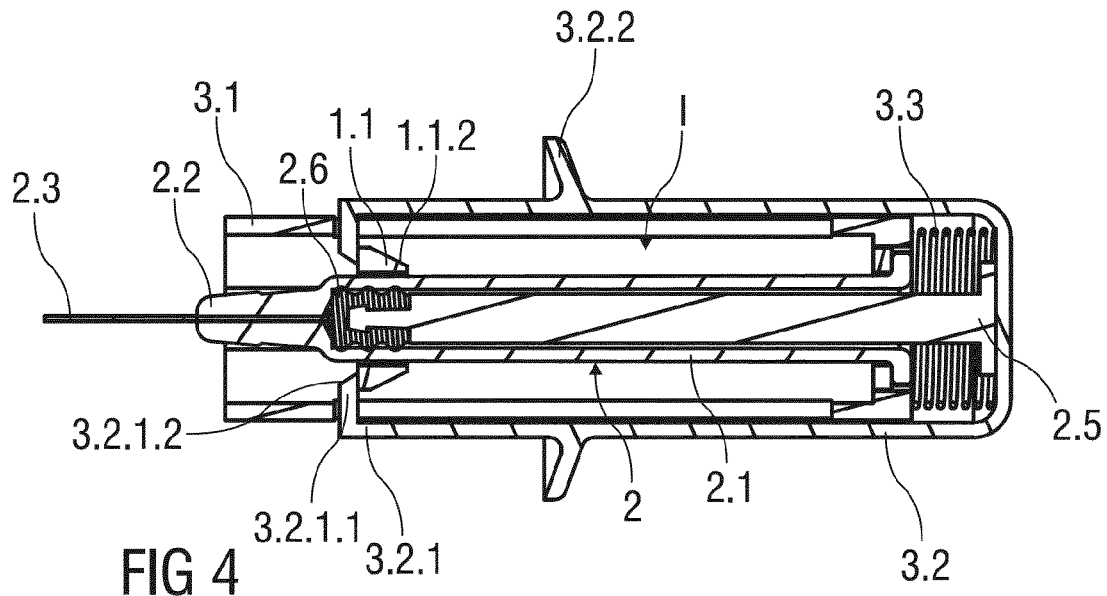
FIG. 4 shows a sectional view of an injection device at the end of an injection stroke.

FIG. 4 shows a sectional view of the injection device D at the end of the injection stroke. The support body 3.1 is substantially received within the hollow outer body 3.2. The spring means 3.3 is fully energized and charged, so that the outer body 3.2 is strongly biased with respect to the support body 3.1 in the proximal direction. The piston rod 2.4 is fully depressed into the barrel 2.1. The radial projection 3.2.1.1 engages the distal collar 1.1, so that the adaptor means 1 with the pre-filled syringe 2 affixed thereto may be retracted from the first position I in the proximal direction by a proximal movement of the outer body 3.2 with respect to the support body 3.1.

The distal collar 1.1 comprises a first tapered flank 1.1.2 that corresponds to a second tapered flank 3.2.1.2 of the radial projection 3.2.1.1. The first and second tapered flanks 1.1.2, 3.2.1.2 allow the radial projection 3.2.1.1 to pass the distal collar 1.1 in the distal direction, whereby the flexible arm 3.2.1 is deflected in a radial outward direction.

Figure 5:
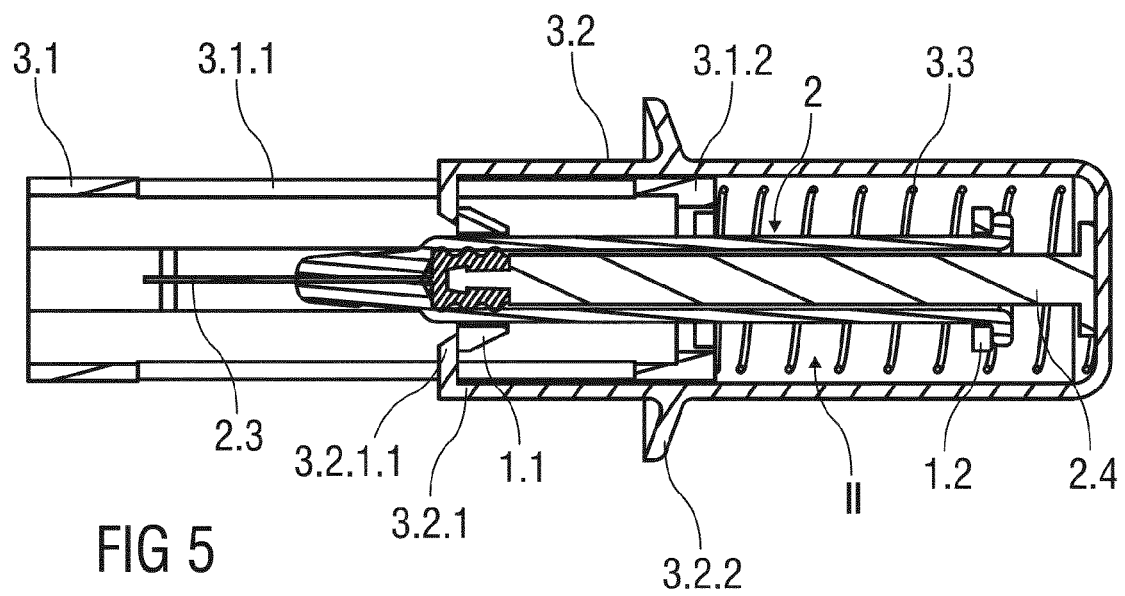
FIG. 5 shows a first sectional view of an injection device with a pre-filled syringe affixed to an adaptor means retained in a second position.

FIG. 5 shows a first sectional view of the injection device D after the injection has been carried out. The adaptor means 1 with the pre-filled 2 affixed thereto is retained in a retracted second position II, wherein the hypodermic needle 2.3 of the pre-filled syringe is surrounded by the support body 3.1. The spring means 3.3 is in a non-energized or only slightly energized state.

Figure 6:
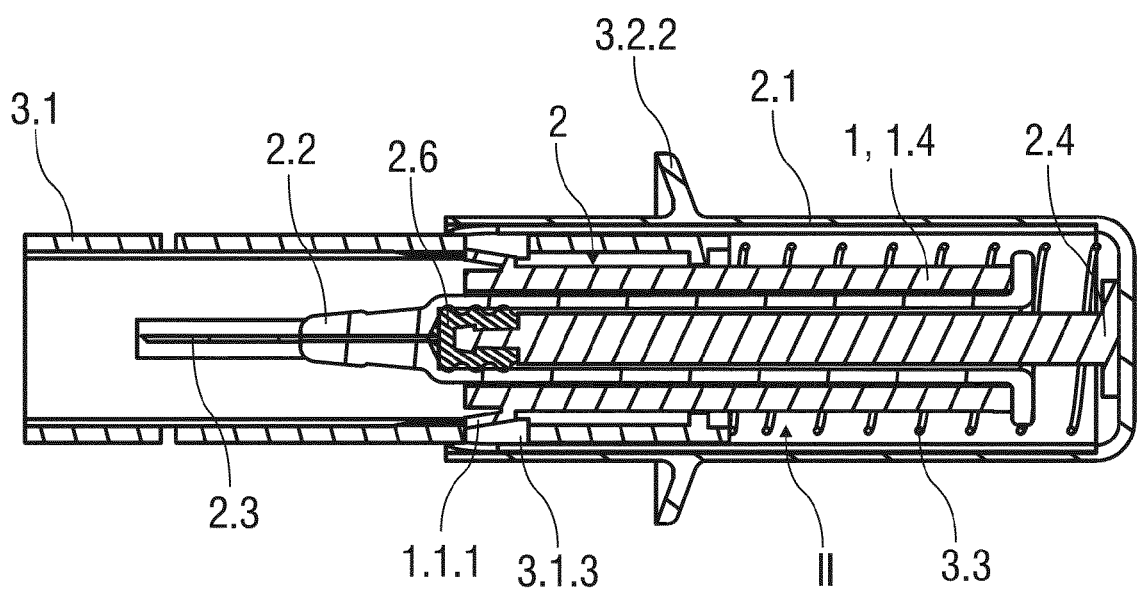
FIG. 6 shows a second sectional view of an injection device with a pre-filled syringe affixed to an adaptor means retained in a second position.

FIG. 6 shows a second sectional view of the injection device D. The sectional plane shown in FIG. 6 is rotated with respect to the first sectional view about an angle of approximately 90 degrees around the axis of the substantially cylindrical safety device 3. The locking projection 1.1.1 of the adaptor means 1 latches to a locking recess 3.1.3 formed into the support body 3.1 to permanently lock the adaptor means 1 and the pre-filled syringe 2 affixed thereto in the second position II. A re-exposure of the hypodermic needle 2.3 of the pre-filled syringe 2 is thus prevented by the locking projection 1.1.1 engaging the locking recess 3.1.3.

The locking projection 1.1.1 engaging the locking recess 3.1.3 is surrounded by the outer body 3.2 and is inaccessible from outside. This prevents a person from tampering with the locking projection 1.1.1 to unlock the adaptor means 1 from being retained in the second position II. The movement of the outer body 3.2 with respect to the support body 3.1 is limited by the radial projection 3.2.1.1 abutting a proximal end of the longitudinal slot 3.1.1, which prevents an exposure of the locking projection 1.1.1 and the locking recess 3.1.3.

The injection is carried out as follows:

After removal of the needle cap 2.5, the hypodermic needle 2.3 is inserted into the skin of the patient. The flange (not illustrated) that provides an increased surface area may rest onto the skin of the patient to facilitate the injection of the medication or drug. The outer body 3.2 is pushed distally towards the skin of the patient to perform the injection stroke, whereby the outer body 3.2 moves with respect to the support body 3.1 in a linear translatory movement. The piston 2.6 jointly moves with the outer body 3.2 in the distal direction to dispose the medication contained in the inner cavity 2.1.2 beneath the skin of the patient.

At the end of the injection stroke the medication is completely disposed and the spring means 3.3 is fully energized. The radial projection 3.2.1.1 clamps to the distal collar 1.1.

Upon removal of the injection device D from the injection site, the spring means 3.3 relaxes, whereby the outer body 3.2 moves proximally to retract the adaptor means 1 together with the pre-filled syringe 2 from the first position I to the second position II.

In the second position II, the locking projection 1.1.1 engages the locking recess 3.1.3 to irreversibly lock the adaptor means 1 and the pre-filled syringe 2 to the second position II, so that a subsequent exposure of the hypodermic needle 2.3 is prevented.

The invention claimed:

1. An injection device comprising a pre-filled syringe and a safety device for the pre-filled syringe, wherein the safety device comprises:
    an adaptor means,
    a hollow support body, and
    a hollow outer body slidably arranged with respect to the hollow support body, wherein a proximal surface of the hollow outer body is arranged to abut a piston rod connected to a piston of the pre-filled syringe, so that the piston rod and the piston may be moved by manually pushing the hollow outer body in a distal direction,
    wherein the adaptor means is adapted to affix the pre-filled syringe thereto, whereby the adaptor means engages a barrel of the pre-filled syringe and wherein the adaptor means comprises at least one locking projection that is adapted to lock the adaptor means to the hollow support body,
    wherein the adaptor means is retained within the hollow support body in a manner that the adaptor means, comprising a retraction mechanism that couples the adaptor means to the hollow outer body through a longitudinal slot in the hollow support body, is movable with respect to the hollow support body by a proximal movement of the hollow outer body with respect to the hollow support body from a first position, in which a hypodermic needle of the pre-filled syringe projects distally from the hollow support body, to a second position, in which the hypodermic needle is surrounded by the hollow support body,
    wherein the at least one locking projection of the adaptor means engages a locking recess formed into the hollow support body to irreversibly lock the adaptor means in the second position.

2. The injection device according to claim 1, wherein the adaptor means has an axial dimension substantially corresponding to an axial length of the barrel of the pre-filled syringe.

3. The injection device according to claim 2, wherein two opposing clamp arms of the adaptor means are adapted to frictionally engage the barrel of the pre-filled syringe to affix the pre-filled syringe to the adaptor means.

4. The injection device according to claim 2, wherein the adaptor means comprises a central aperture with an inner diameter corresponding to an outer diameter of the barrel of the pre-filled syringe.

5. The injection device according to claim 2, wherein the adaptor means comprises a proximal collar adapted to abut a barrel collar of the barrel.

6. The injection device according to claim 1, wherein the at least one locking projection comprises a plurality of locking projections projecting radially outwards from two opposite sides of the adaptor means.

7. The injection device according to claim 1, wherein the retraction mechanism comprises a radial projection of the hollow outer body protruding radially inwards through the longitudinal slot, wherein the radial projection catches a distal collar of the adaptor means to couple the adaptor means to the hollow outer body.

8. The injection device according to claim 7, wherein the adaptor means coupled to the hollow outer body is movable from the first position to the second position by a proximal movement of the hollow outer body with respect to the hollow support body.

9. The injection device according to claim 1, wherein a spring means is arranged within the safety device to bias the hollow outer body with respect to the hollow support body in a proximal direction.

10. The injection device according to claim 9, wherein the spring means is arranged within the safety device in a non-energized or only slightly energized state.

11. The injection device according to claim 1, wherein the hollow outer body is moveable with respect to the hollow support body in the distal direction to perform an injection stroke, whereby a medication or drug contained in an inner cavity of the pre-filled syringe is expelled through the hypodermic needle.

* * * * *